United States Patent [19]
Hase et al.

[11] 4,057,622
[45] Nov. 8, 1977

[54] WATER-IN-OIL CREAMS WITH POLYMERIC EMULSIFIERS

[75] Inventors: Brigitte Hase; Christian Hase, both of Erkrath; Joachim Galinke, Langenfeld; Bernd Wegemund, Haan, all of Germany

[73] Assignee: Henkel Kommanditgesellschaft auf Aktien, Dusseldorf, Germany

[21] Appl. No.: 670,362

[22] Filed: Mar. 25, 1976

[30] Foreign Application Priority Data

Mar. 29, 1975 Germany .............................. 2514101

[51] Int. Cl.² ............................................. A61K 31/74
[52] U.S. Cl. ............................... 424/78; 424/DIG. 2; 424/168
[58] Field of Search .................... 424/78, 168, DIG. 2

[56] References Cited

U.S. PATENT DOCUMENTS

| 3,773,926 | 11/1973 | Knowles et al. | 424/78 |
| 3,937,811 | 2/1976 | Papantoniou et al. | 424/78 X |
| 3,954,682 | 5/1976 | Fein et al. | 424/78 X |

FOREIGN PATENT DOCUMENTS

| 2,116,787 | 10/1971 | Germany | 424/78 |

Primary Examiner—Dale R. Ore
Attorney, Agent, or Firm—Hammond & Littell

[57] ABSTRACT

Cosmetic emulsions containing from 2 to 20% by weight of polymeric emulsifiers capable of forming water-in-oil creams comprising a copolymer of N-vinylimidazole, an alkyl (meth)acrylate and optionally vinyl acetate; 20 to 75% by weight of water; and the remainder to 100% by weight of a cosmetically-acceptable oily substance.

7 Claims, No Drawings

4,057,622

WATER-IN-OIL CREAMS WITH POLYMERIC EMULSIFIERS

RELATED ART

In contrast to the production of oil-in-water emulsions, only a limited number of emulsifying agents are available, the best of which are becoming increasingly scarce, for producing cosmetic emulsions of the water-in-oil type. Wool fat and its derivatives are still some of the most important emulsifying agents for producing creams of the water-in-oil type. However, despite their uncontested advantages, wool fat and its derivatives such as lanolin have certain disadvantages. Thus, conventional water-in-oil emulsifying agents based on wool fat and its derivatives impart a strong intrinsic odor to the creams produced from them. This, in turn, requires strong perfuming which frequently cannot be tolerated by persons with sensitive skin. However, this influencing of the quality of the cream by a strong intrinsic odor is not only peculiar to wool fat and its derivatives, but also extends to lanolin-free water-in-oil emulsifying agents based on animal sterols, particularly those based on cholesterol. Furthermore, low-molecular weight emulsifying agents, together with the effective substances of the cream, can be absorbed by the skin, which is not desirable in all cases.

The most widely known water-in-oil emulsifying agents for cosmetic purposes include, in addition to the said emulsifying agents based on wool, the wax alcohols and sterols, the oleic acid esters of various polyols such as glycerine, pentaerythritol, trimethylolpropane and sorbitol. However, due to the unsaturated character of their acid component, the oleic acid esters have various disadvantages with respect to their technical use, so that there is a genuine need for new and suitable water-in-oil emulsifying agents.

OBJECTS OF THE INVENTION

An object of the present invention is the production of a cosmetic emulsion of the water-in-oil type consisting essentially of (1) from 2% to 20% by weight of a polymeric emulsifier capable of forming water-in-oil creams consisting of a copolymer of (a) N-vinylimidazole, (b) acrylates of the formula

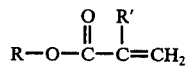

wherein R is a member having from 6 to 24 carbon atoms selected from the group consisting of alkyl, cycloalkyl and alkylcycloalkyl, and R' is a member selected from the group consisting of hydrogen and methyl, and (c) vinyl acetate wherein the molar ratios of (a) + (c) : (b) are from 1:1 to 1:20 and the molar ratios of (c) : (a) are 0:1 to 3:1, (2) from 20% to 75% by weight of water and (3) the remainder to 100% by weight of a cosmetically-acceptable oily phase.

These and other objects of the present invention will become more apparent as the description thereof proceeds.

DESCRIPTION OF THE INVENTION

It has now been discovered that the objections of the prior emulsifiers have been overcome and the above objects have been achieved by the discovery of cosmetic emulsions of the water-in-oil type having a content of a copolymer or terpolymer from N-vinylimidazole, an alkyl (meth)acrylate having 6 to 24 carbon atoms in the alkyl- or cycloalkyl radical and, if required, vinyl acetate, in a quantity of from 2% to 20% by weight, a quantity of from 20% to 75% by weight of water, relative to the total emulsion, and vegetable or animal fats, waxes, fatty alcohols, hydrocarbons and further auxiliary substances normally used in cosmetic emulsions.

More particularly, the present invention relates to a cosmetic emulsion of the water-in-oil type consisting essentially of (1) from 2% to 20% by weight of a polymeric emulsifier capable of forming water-in-oil creams consisting of a copolymer of (a) N-vinylimidazole, (b) acrylates of the formula

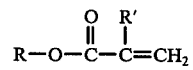

wherein R is a member having from 6 to 24 carbon atoms selected from the group consisting of alkyl, cycloalkyl and alkylcycloalkyl, and R' is a member selected from the group consisting of hydrogen and methyl, and (c) vinyl acetate wherein the molar ratios of (a) + (c) : (b) are from 1:1 to 1:20 and the molar ratios of (c) : (a) are 0:1 to 3:1, (2) from 20% to 75% by weight of water and (3) the remainder to 100% by weight of a cosmetically-acceptable oily phase.

The copolymers of terpolymers from N-vinylimidazole, alkyl (meth)acrylates and, if required, vinyl acetate, usable as emulsifying agents in the cosmetic emulsions in accordance with the invention, can be produced in a generally known manner by one processing step under the normal conditions of free radical polymerization. Polymerization can be carried out in nonpolar solvents such as benzene or toluene or in polar solvents such as methanol or tetrahydrofuran, by means of peroxides such as dibenzoyl peroxide or lauroyl peroxide and azo compounds such as azobisisobutyronitrile as free-radical polymerization catalysts.

The technical production is effected to best advantage in the form of solution polymerization in such solvents which only dissolve the monomers but not the polymers produced (precipitation polymerization), especially since polymers are produced which are satisfactorily precipitable and which are virtually free from monomers (J. Scheiber, Chemie und Technologie der kunstlichen Harze, Vol. I, pages 362 ff, 1961).

Monomeric starting compounds of the polymeric emulsifier which may be mentioned in addition to N-vinylimidazole and, if required, vinyl acetate, are, for example, hexyl acrylte, octyl acrylate, 2-ethylhexyl acrylate, nonyl acrylate, decyl acrylate, lauryl acrylate, myristyl acrylate, cetyl acrylate, stearyl acrylate, oleyl acrylate, behenyl acrylate, tert.butylcyclohexyl acrylate, hexyl methacrylate, octyl methacrylate, nonyl methacrylate, decyl methacrylate, lauryl methacrylate, myristyl methacrylate, cetyl methacrylate, stearyl methacrylate, oleyl methacrylate, behenyl methacrylate, etc. Particular importance is attached to the acrylic or methacrylic acid esters of the fatty alcohols having 8 to 14 carbon atoms, such as octyl acrylate, nonyl acrylate, decyl acrylate, lauryl acrylate, myristyl acrylate, octyl methacrylate, nonyl methacrylate, decyl methacrylate, lauryl methacrylate, and myristyl methacrylate.

In the copolymers or terpolymers usable in accordance with the invention, the molar ratios of the monomers N-vinylimidazole + (vinylacetate): alkyl (meth)acrylate are 1:1 to 1:20, preferably 1:3 to 1:12, wherein the molar ratios of vinylacetate/N-vinylimidazole can assume values of 0 to 3.

The copolymers of terpolymers which may be used in accordance with the invention also include those in which the imidazole radical is present partially or fully in the form of imidazolium salts with organic or inorganic acids, for example, in the form of imidazolinium lactate.

The copolymers or terpolymers usable in accordance with the invention have average molecular weights between 2000 and 100,000; those having average molecular weights between 3000 and 20,000 are particularly suitable in view of the easy processability and the quality of the emulsions obtained. These molecular weights can be adjusted in a known manner by the amount of catalyst, the nature and amount of the solvent, and by adding polymerization or molecular weight regulators.

The emulsions in accordance with the invention are manufactured in a simple and known manner by dissolving the copolymers or terpolymers, acting as emulsifying agents, in the oily phase at an increased temperature of approximately 60° to 70° C. Subsequently the desired quantity of water heated to approximately 60° to 65° C is added, and the emulsion obtained is stirred while cooling. Further constituents of the cosmetic emulsions to be manufactured, such as skin moisture regulators, vegetable extracts of effective substances, vitamins, hormones, pigments, salts, perfume oil, UV filtering media, dyestuffs, etc., are advantageously dissolved or distributed in the phase which absorbs these substances to best advantage. The required quantity of emulsifying agent is 2% to b 20% by weight, preferably 5% to 10% by weight, relative to the total cosmetic emulsion. The amount of water to be incorporated can be 20% to 75% by weight, preferably 45% to 65% by weight, preferably 45% to 65% by weight, relative to the total cosmetic emulsion.

Products conventionally used, such as animal and vegetable oils and fats, synthetic esters of higher fatty acids with alkanols, higher fatty alcohols, waxes, so-called mineral fats and oils such as paraffin oil, "Vaseline ®", ceresine, silicone oils and silicone fats are suitable as the oily phase of the cosmetic emulsions in accordance with the invention. Preferably, they should have melting points about 30° C and be substantially solids at room temperature. The oily phase represents the remainder up to 100% by weight of the total cosmetic emulsion.

German Offenlegungsschrift (DOS) No. 2,116,787 has already described the use of water-in-oil emulsifying agents in the form of sequence polymers which have at the same time at least one lipophilic sequence and one hydrophilic sequence. Each of the sequences should have the properties of the corresponding homopolymers. These sequence polymers are obtained by anionic polymerization which places high demandson the purity of the substances used, and requires working at low temperatures under protective gas and increased safety precautions when handling spontaneously inflammable catalysts. In contrast to this, the emulsifying agents required for producing the emulsions in accordance with the present invention can be manufactured in a simple manner.

In accordance with German Offenlegungsschrift (DOS) No. 1,745,216, copolymers comprising a monomer having a lipophilic chain and a monomer having a carboxylic acid anhydride function are proposed as emulsifying agents for water-in-oil emulsions. However, such products are sensitive to hydrolysis and, to avoid this disadvantage, a further processing step in addition to polymerization is necessary in order to convert them into a more stable form.

In general, the emulsions in accordance with the present invention can also be used by persons having a sensitive skin. Since they do not have any appreciable intrinsic odor, they do not require heavy perfuming which, in turn, has an advantageous effect upon the compatibiliy and also saves costs.

Furthermore, the emulsions in accordance with the invention are distinguished by a low sensitivity to acid, thus rendering it possible to incorporate acidic raw materials therein, such as organic acids. A further very advantageous property of the emulsions in accordance with the invention is their high resistance to temperature, which enables them to withstand a thermal stress of 50° C for a period of 6 weeks without any detrimental effects.

The following Examples are intended to further explain the invention, but without limiting the invention to these Examples.

EXAMPLES

The production of a copolymer which may be used in the cosmetic emulsions in accordance with the invention will be described in the first instance.

EXAMPLE 1

N-Vinylimidazole/Lauryl Acrylate Copolymer (1:3)

23.5 gm (0.25 mol) of N-vinylimidazole and 179.75 gm (0.75 mol) of lauryl acrylate were dissolved in 480 gm of toluene. 4 gm of dibenzoylperoxide were added as a catalyst to the solution obtained. The reaction mixture was agitated for 6 hours at 60° C. After the reaction had been completed, the solvent was distilled off and the product was washed a few times with methanol. 162 gm, that is 80% of theory, of N-vinylimidazole/lauryl acrylate copolymer (1:3) were obtained.

The other copolymers or terpolymers, used in the Examples given below, were obtained in an analogous manner.

EXAMPLE 2

Cosmetic Emulsions Based on "Vaseline ®"

A mixture of 10 gm of N-vinylimidazole/lauryl acrylate copolymer (1:3)
40 gm of "Vaseline ®"

were melted together by heating to 65° C.

50 gm of water, which had been heated to 65° C, were added to the melt, and the mass was allowed to cool with constant agitation. The emulsion can be readily produced by manual stirring. The cream obtained in stable for several months and did not exhibit any change even when held at 50° C for 6 weeks. This basic cream can be used to produce various skin creams by further adding various effective substances and perfume oils.

"Vaseline ®" is a purified mixture of semi-solid hydrocarbons; petrolatum.

By way of example, the following copolymers can be used with the same satisfactory result instead of the N-vinylimidazole/lauryl acrylate copolymer (1:3):

| | Molar Ratio |
|---|---|
| N-vinylimidazole/lauryl acrylate copolymer | (1:6) |
| N-vinylimidazole/nonyl methacrylate copolymer | (1:15) |
| N-vinylimidazole/octyl acrylate copolymer | (1:20) |
| N-vinylimidazole/decyl methacrylate copolymer | (1:8) |
| N-vinylimidazole/decyl acrylate copolymer | (1:10) |
| N-vinylimidazole/myristyl methacrylate copolymer | (1:4) |
| N-vinylimidazole/lauryl methacrylate copolymer | (1:6) |
| N-vinylimidazole/cetyl acrylate copolymer | (1:5) |
| N-vinylimidazole/stearyl methacrylate copolymer | (1:2) |
| N-vinylimidazole/2-ethylhexyl methacrylate copolymer | (1:10) |

EXAMPLE 3

Cosmetic Emulsion Based on Hardened Peanut Oil/Decyl Oleate

A mixture of 4 gm of N-vinylimidazole/decyl acrylate copolymer (1:6 molar ratio)
40 gm of hardened peanut oil/decyl oleate mixture (90:10)
3 gm of bees-wax
3gm of glyceryl monooleate were melted together by hearing to 70° C.

50 gm of water, which had been heated to 65° C, were added to the melt under continuous agitation, and the mass was allowed to cool under further agitation. A cream was obtained whose stability properties are largely similar to those of the cream of Example 2. Various skin creams based on this basic cream can be produced by incorporating further effective substances such as skin moisture regulators, vegetable extracts, and perfume oils.

By way of example, the following copolymers can be used with the same satisfactory result instead of the N-vinylimidazole/decyl acrylate copolymer (1:6):

| | Molar Ratio |
|---|---|
| N-vinylimidazole/myristyl methacrylate copolymer | (1:3) |
| N-vinylimidazole/lauryl methacrylate copolymer | (1:5) |
| N-vinylimidazole/lauryl acrylate copolymer | (1:8) |
| N-vinylimidazole/octyl acrylate copolymer | (1:10) |
| N-vinylimidazole/cetyl methacrylate copolymer | (1:4) |
| N-vinylimidazole/behenyl acrylate copolymer | (1:2) |
| N-vinylimidazole/lauryl-myristyl acrylate copolymer | (1:6) |
| N-vinylimidazole/tert.butylcyclohexyl acrylate copolymer | (1:8) |

EXAMPLE 4

Cosmetic Emulsions based on "Vaseline ®"/Decyl Oleate Mixture

A mixture of 7 gm N-vinylimidazole/vinyl acetate/lauryl-myristyl acrylate terpolymer (2:1:10 molar ratio)
10 gm of "Vaseline ®"
15 gm of decyl oleate
3 gm of bees-wax
2 gm of calcium stearate were fused together by heating to 65° C.

63 gm of water, heated to 65° C, were stirred into this mixture and agitation was continued until the emulsion was cold. A cream was obtained whose stability properties are largely similar to those of the two creams described above. A large number of cosmetic creams based on this basic cream can be produced by incorporating cosmetic effective substances and perfume oils. "Vaseline ®" is a purified mixture of semi-solid hydrocarbons; petrolatum. Lauryl-muristyl is a mixed fatty alcohol.

By way of example, the following terpolymers may be used with the same satisfactory result instead of the N-vinylimidazole/vinyl acetate/ lauryl-myristyl acrylate terpolymer (2:1:10):

| | Molar Ratio |
|---|---|
| N-vinylimidazole/vinyl acetate/lauryl acrylate terpolymer | (3:1:12) |
| N-vinylimidazole/vinyl acetate/octyl methacrylate terpolymer | (2:1:15) |
| N-vinylimidazole/vinyl acetate/myristyl acrylate terpolymer | (1:2:10) |
| N-vinylimidazole/vinyl acetate/myristyl methacrylate terpolymer | (1:3:8) |
| N-vinylimidazole/vinyl acetate/lauryl acrylate terpolymer | (1:1:10) |
| N-vinylimidazole/vinyl acetate/decyl acrylate terpolymer | (1:1:12) |
| N-vinylimidazole/vinyl acetate/lauryl-myristyl acrylate terpolymer | (2:1:6) |
| N-vinylimidazole/vinyl acetate/lauryl methacrylate terpolymer | (4:1:15) |

EXAMPLE 5

Cosmetic Emulsions Based on Hardened Peanut Oil

A mixture of 6 gm of N-vinylimidazole/vinyl acetate/lauryl-myristyl acrylate terpolymer (4:1:20 molar ratio)
44 gm of hardened peanut oil were melted together by heating to 65° C.

50 gm of water, heated to 65° C, were stirred into this mixture. After agitation until cool, a cream was obtained whose stability properties are largely similar to the previously mentioned creams.

The cream can act as a basic cream for various cosmetic preparations.

By way of example, the following terpolymers can be used with the same satisfactory result instead of the N-vinylimidazole/vinyl acetate/lauryl-myristyl acrylate terpolymer (4:1:20):

| | Molar Ratio |
|---|---|
| N-vinylimidazole/vinyl acetate/lauryl methacrylate terpolymer | (1:2:10) |
| N-vinylimidazole/vinyl acetate/myristyl acrylate terpolymer | (3:1:12) |
| N-vinylimidazole/vinyl acetate/decyl acrylate terpolymer | (2:1:15) |

The preceding specific embodiments are illustrative of the practice of the invention. It is to be understood, however, that other expiedents known to those skilled in the art or disclosed herein, may be employed without departing from the spirit of the invention or the scope of the appended claims.

We claim:

1. A cosmetic emulsion of the water-in-oil type consisting essentially of (1) from 2% to 20% by weight of a polymeric emulsifier capable of forming water-in-oil creams selected from the group consisting of (i) a copolymer of (a) N-vinylimidazole, (b) acrylates of the formula

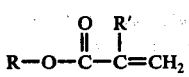

wherein R is a member having from 6 to 24 carbon atoms selected from the group consisting of alkyl, cycloalkyl, alkylcycloalkyl and oleyl, and R' is a member selected from the group consisting of hydrogen and methyl, and (c) vinyl acetate wherein the molar ratios of (a) + (c) : (b) are from 1:1 to 1:20 and the molar ratios of (c) : (a) are 0:1 to 3:1, and (ii) salts thereof with organic or inorganic acids, (2) from 20% to 75% by weight of water and (3) the remainder to 100% by weight of a cosmetically-acceptable oily phase.

2. The cosmetic emulsion of claim 1 wherein said cosmetically-acceptable oily phase has a melting point above 30° C and is selected from the group consisting of vegetable fat, animal fat, wax, higher fatty alcohol, mineral oil and silicone oil.

3. The cosmetic emulsion of claim 1 wherein said polymeric emulsifier is present in an amount of from 5% to 10% by weight and said water is present in an amount of from 45% to 65% by weight.

4. The cosmetic emulsion of claim 1 wherein R is alkyl having from 8 to 14 carbon atoms.

5. The cosmetic emulsion of claim 1 wherein the molar ratio of (a) + (c) : (b) is from 1:3 to 1:12.

6. The cosmetic emulsion of claim 1 wherein said polymeric emulsifier has an average molecular weight of from 2000 to 100,000.

7. The cosmetic emulsion of claim 6 wherein said average molecular weight is from 3000 to 20,000.

* * * * *